(12) United States Patent
Sommer

(10) Patent No.: US 7,611,353 B2
(45) Date of Patent: Nov. 3, 2009

(54) SELF-LIGATING BRACKET SYSTEM

(75) Inventor: Jay S. Sommer, Howards Grove, WI (US)

(73) Assignee: American Orthodontics Corporation, Sheboygan, WI (US)

( * ) Notice: Subject to any disclaimer, the term of this patent is extended or adjusted under 35 U.S.C. 154(b) by 0 days.

(21) Appl. No.: 11/529,063

(22) Filed: Sep. 28, 2006

(65) Prior Publication Data

US 2007/0072143 A1   Mar. 29, 2007

Related U.S. Application Data

(60) Provisional application No. 60/721,392, filed on Sep. 28, 2005.

(51) Int. Cl.
*A61C 3/00*   (2006.01)

(52) U.S. Cl. ........................................ 433/10

(58) Field of Classification Search ................ 433/8–17
See application file for complete search history.

(56) References Cited

U.S. PATENT DOCUMENTS

| | | | |
|---|---|---|---|
| 4,492,573 A | 1/1985 | Hanson | 433/11 |
| 5,711,666 A | 1/1998 | Hanson | 433/11 |
| 5,906,486 A | 5/1999 | Hanson | 433/11 |
| 5,908,293 A * | 6/1999 | Voudouris | 433/10 |
| 5,913,680 A | 6/1999 | Voudouris | 433/10 |
| 6,071,118 A * | 6/2000 | Damon | 433/9 |
| 6,071,119 A | 6/2000 | Christoff et al. | 433/14 |
| 2002/0132206 A1* | 9/2002 | Voudouris | 433/11 |
| 2004/0166457 A1* | 8/2004 | Devincenzo | 433/8 |
| 2004/0170942 A1* | 9/2004 | Heiser | 433/11 |
| 2007/0160949 A1* | 7/2007 | Voudouris | 433/8 |

* cited by examiner

*Primary Examiner*—Ralph A Lewis
*Assistant Examiner*—Sunil K Singh
(74) *Attorney, Agent, or Firm*—Philip G. Meyers

(57) ABSTRACT

An orthodontic bracket system includes a bracket and a clip. During closing, an arm of the clip rides down against an inclined rear surface of a first tie wing and a portion of the clip bends resiliently, exerting a force that locks a locking edge portion of the clip in a recess beneath second tie wings. During opening, the arm rides up against the inclined rear surface of the first tie wing as the locking edge portion of the clip is removed from the recess beneath the second tie wings. The clip is then moved to an open position to permit placement and removal of the archwire and held in that position.

5 Claims, 7 Drawing Sheets

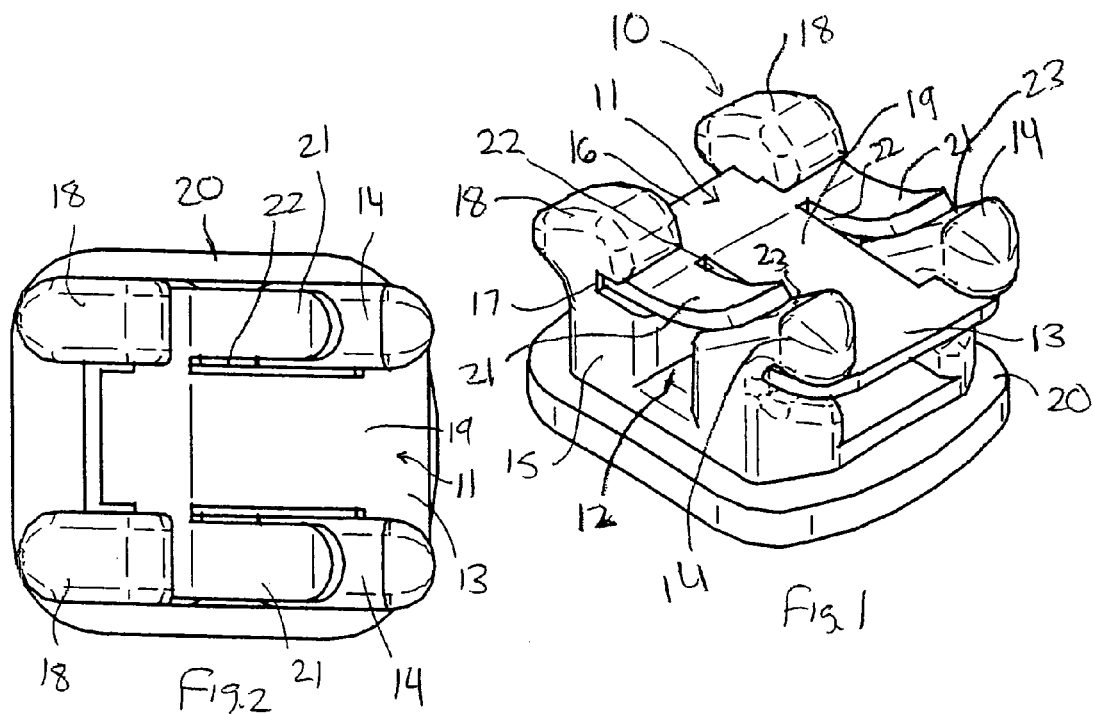
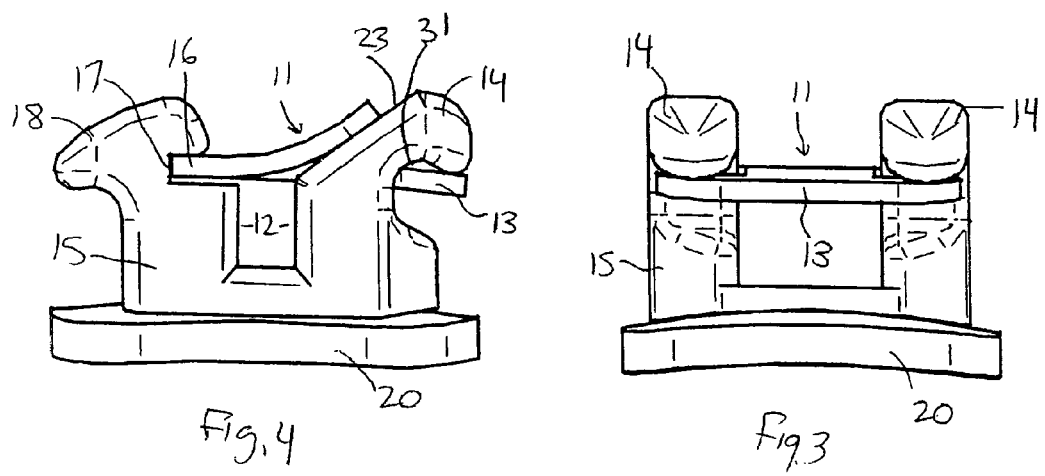

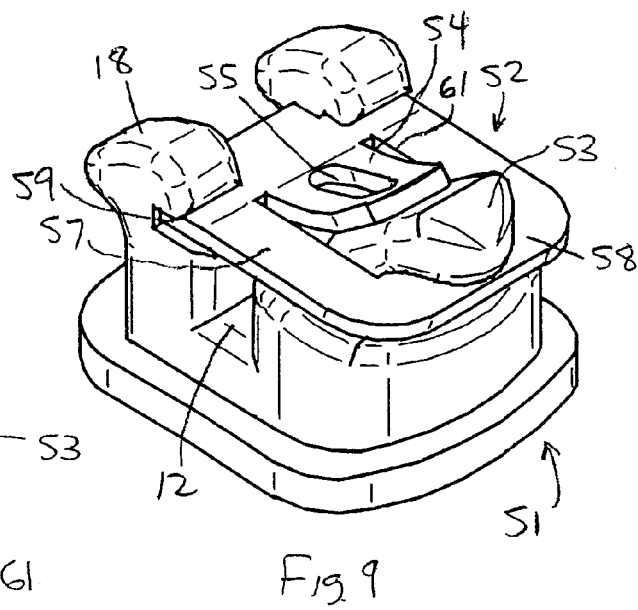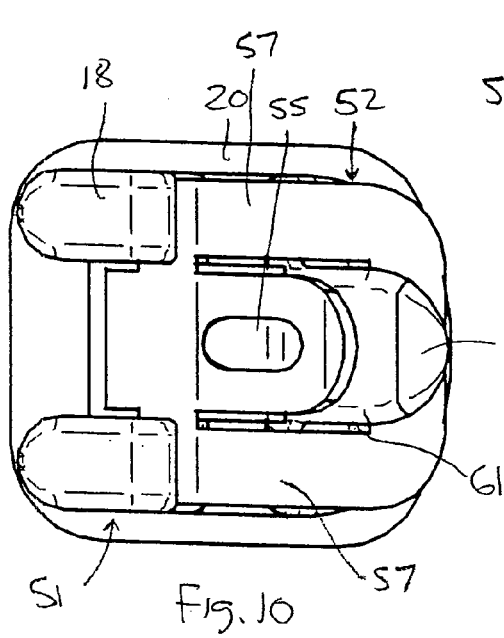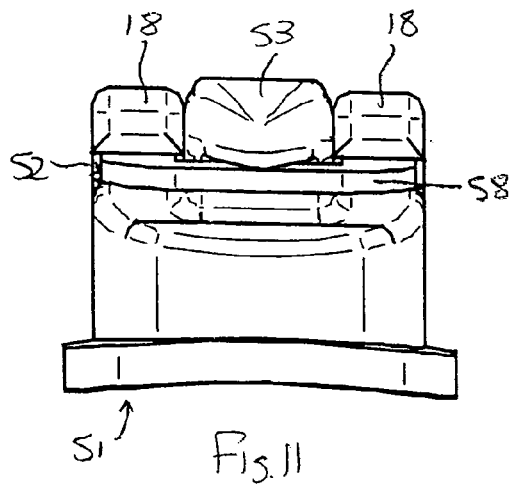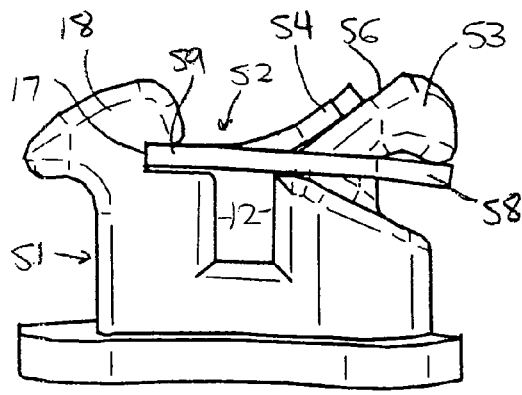

SELF-LIGATING BRACKET SYSTEM

This application claims priority of U.S. Provisional Application No. 60/721,392, filed Sep. 28, 2005.

TECHNICAL FIELD

The invention relates to brackets used in orthodontic treatment, more specifically to an orthodontic bracket having a clip or latch for releasably retaining an archwire in an archwire slot of the bracket.

BACKGROUND OF THE INVENTION

During one type of common orthodontic treatment, a series of small brackets are fixed to a patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth. Many types of orthodontic brackets have archwire slots that are open on one side for insertion of the archwire, and confined on remaining sides by the bracket tie wings or other structure. Brackets bonded to the patient's front tooth surfaces often have archwire slots that open on a buccolabial side (facing the patient's cheeks or lips) or an occlusal side (facing the outer tips of the teeth) of the archwire slot.

Ligatures such as elastomeric O-rings are commonly used to connect the archwire to each bracket and to urge the archwire into seating engagement in the archwire slot. However, ligatures are time-consuming to install, decay over time and can become stained and unsightly. As a result self-ligating brackets were developed wherein each bracket has a clip or latch mounted thereon for retaining an archwire in the archwire slot. Christoff et al. U.S. Pat. No. 6,071,119, describes one such self-ligating bracket and contains an extended discussion of different types of known self-ligating bracket system in its background section. Voudouris U.S. Pat. Nos. 5,908,293 and 5,913,680, among others, illustrate that a wide variety of self-ligating bracket structures have been proposed.

Most known self-ligating bracket systems do not require complete removal of the clip when it is necessary to access the archwire slot. The clip or shutter can assume open and closed positions without being fully removed from the bracket. Known U-shaped clips slide into and out of these positions and use some form of detent to hold the clip in the open position. In the open position, the archwire slot is accessible, but the clip has not been fully removed from the bracket.

Build-up of calculus over time can make it difficult to remove shutters or clips that slide into and out of place, such as of the detent style. Hinged designs avoid this problem, but it is also desirable to avoid elaborate structures such as built-in hinges where possible, while still providing a clip that performs reliably, is easy to use and inexpensive to manufacture. The present invention addresses these needs.

SUMMARY OF THE INVENTION

An orthodontic bracket system according to the invention includes a bracket having a base contoured to engage a tooth surface, a body extending from the base, at least one first tie wing connected to the body, and a pair of second tie wings connected to the body and spaced from the first tie wing in an occlusal-gingival direction when the bracket is mounted on a tooth. An archwire slot extends between the first and second tie wings in a mesial-distal direction, wherein the first tie wing has an outwardly inclined rear surface proximate the archwire slot. A clip for use with the bracket has a retaining portion configured to fit beneath the first tie wing on the side thereof opposite the archwire slot, a locking edge portion remote from the retaining portion that fits into a recess beneath the second tie wings, a mid-portion that spans the retaining portion and the locking edge portion and covers at least a portion of the archwire slot in a manner effective to retain an archwire therein, and at least one arm that extends from the locking edge portion towards the retaining portion and is spaced from the mid-portion. During closing, the arm rides down against the inclined rear surface of the first tie wing and a portion of the clip (e.g., the arm, the mid-portion or both) bends resiliently, exerting a force that locks the locking edge portion of the clip in the recess beneath the second tie wings. During opening, the arm rides up against the inclined rear surface of the first tie wing as the locking edge portion of the clip is removed from the recess beneath the second tie wings. The clip is then moved to an open position to permit placement and removal of the archwire, and held in that position.

In preferred forms of the invention, the bracket has two pairs of first and second tie wings, and the clip is configured with two resilient arms that engage inclined outer surfaces of the first tie wings. The clip and first tie wings are also configured so that the clip can assume an open position wherein the archwire slot is accessible, but the clip remains mounted on the bracket in a pivoted-up position.

The invention further provides a clip for use in the foregoing bracket system which before installation comprises a flat, resilient sheet. These and other aspects of the invention are further discussed in the detailed description that follows.

BRIEF DESCRIPTION OF THE DRAWINGS

In the accompanying drawing figures, like numerals denote like elements, and:

FIG. 1 is a perspective view of a bracket system according to a first embodiment of the invention, with the clip in a closed position;

FIG. 2 is a top view of the bracket system shown in FIG. 1;

FIG. 3 is an end view of the bracket system shown in FIG. 1;

FIG. 4 is a side view of the bracket system shown in FIG. 1;

FIG. 9 is a perspective view of a bracket system according to a second embodiment of the invention, with the clip in a closed position;

FIG. 10 is a top view of the bracket system shown in FIG. 9;

FIG. 11 is an end view of the bracket system shown in FIG. 9;

FIG. 12 is a side view of the bracket system shown in FIG. 9;

DETAILED DESCRIPTION

Figure 5:
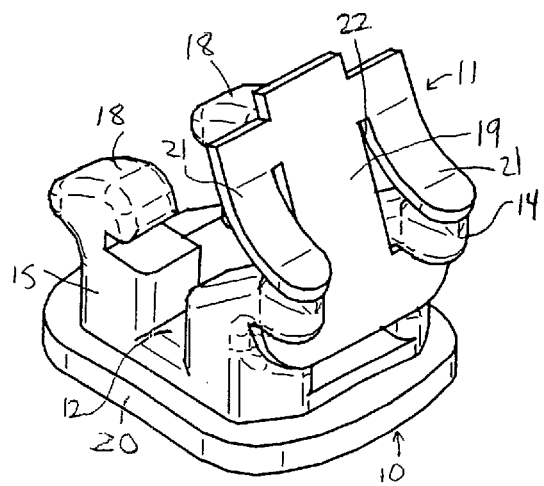
FIG. 5 is a perspective view of the bracket system shown in FIG. 1, with the clip in an open position.
Figure 6:
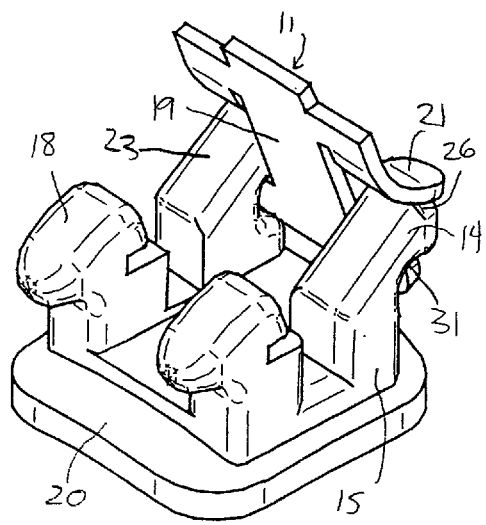
FIG. 6 is the same view as FIG. 5, viewed from a different perspective.

The invention is a self-ligating bracket system that relies on one or more arms or wings to lock the shutter or clip in place. Bracket systems are classified as either passive or active. A passive bracket system traps an archwire in the slot and creates an inflexible barrier when the archwire exerts force against it. An active or interactive bracket system is resilient, i.e. yields to some extent when the archwire moves against it, and exerts a counter force that tends to urge the archwire back into the slot. The examples discussed herein are of the passive type. The clip of the invention is resilient and bends when locking, exerting a resilient force. The resilient force is used to lock the clip, and it becomes a passive type of locking system.

With reference to FIGS. 1 to 8, a self-ligating bracket system of the invention includes a bracket 10 with a body 15 and base 20, and a clip 11 that is removably mounted thereon over the archwire slot 12. The clip 11 of the invention can vary in form and cooperates with several surfaces of the bracket 10 in order to perform its functions. Clip 11 has a retaining portion 13 that configured to fit beneath a first tie wing or pair of gingival tie wings 14. A locking edge portion 16 remote from retaining portion 13 fits into a corresponding slot or recess 17 beneath the other (occlusal) tie wing or pair of tie wings 18. This arrangement is preferred in order to allow the clip 11 to open in a convenient direction for access by the clinician. A mid-portion 19 of clip 11 spans retaining portion 13 and locking edge portion 16, and covers at least an operative portion of the archwire slot 12. One or more resilient arms 21 extend from locking edge portion 16 towards the retaining portion 13 and are spaced from mid-portion 19 by grooves 22, which can vary in size.

The bracket 10 used with clip 11 can vary in design depending on the intended purpose, but has certain features needed to interact with clip 11. The first tie wing(s) 14 have outwardly inclined rear surfaces 23 proximate the archwire slot 12. During and after installation of the clip 11, the resilient arms 21 ride up against these surfaces 23 and bend resiliently, exerting a force which locks the locking edge portion 16 of the clip 11 in slot 17 beneath the second tie wings 18. The mid-portion 19 of the clip 11 remains flat and effectively covers the archwire slot 12. The retaining portion 13 becomes lodged against the undersides of the first tie wings 14. Clip 11 is thereby held securely on both sides of the archwire slot 12.

Figure 7:
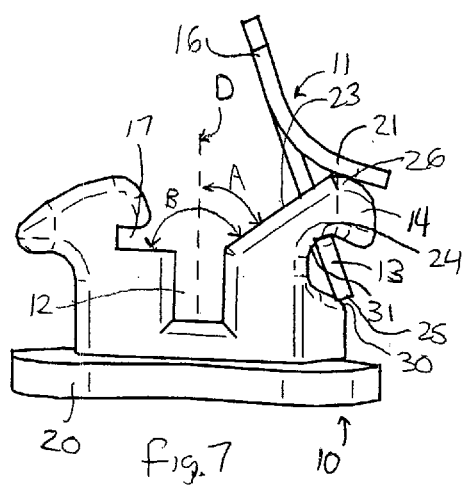
FIG. 7 is a side view of the bracket system shown in FIG. 5.

As shown in FIG. 7, a labial-lingual direction D of the archwire slot forms an acute angle A relative to sloped surface 23 that preferably is in a range from about 45 to 70 degrees (60 degrees in this example.) Angle B between the depthwise dimension of slot 17 and sloped surface 23 is an obtuse angle preferably from about 135 to 160 degrees. Slot 17 is preferably substantially perpendicular to direction D of the archwire slot 12, but could vary several (e.g., up to about 10 degrees) from the orthogonal in either direction. The foregoing configuration confines the archwire securely while preventing excessive or insufficient bending of arms 21. If arms 21 do not bend enough, edge portion 16 may tend to come loose from slot 17. If arms 21 are bent at too harsh an angle during opening and closing, the force required to open clip 11 becomes too great and arms 21 may suffer distortion.

Clip 11 can be opened by lifting an exposed part of the locking edge portion 16 with a tool, pushing the clip 11 back and making the arms 21 ride up further along the inclined rear surfaces 23 of the first tie wings 14. The clip 11, once unlocked by sliding a short distance, can be moved to a position where the archwire slot is open and the clip is held in an open position on the bracket. In this case, clip 11 pivots along an inner edge 24 of retaining portion 13 to a position where resilient arms 21 resiliently engage rounded tops 26 of tie wings 14, holding clip 11 in an open position at an angle of about 60 to 90 degrees relative to its closed position. Rounded tops 26 have a cammed profile effective to hold clip 11 in the open position, i.e., once in the position shown in FIG. 7, the clinician must overcome a retaining force to move clip 11 back to its closed position.

Narrower arms 21 bend more readily, and the shape of clip 11 can be varied as needed to permit the self-ligating bracket to be opened and closed without difficulty, yet remain reliably closed while in use. Arms 21 are the only portion of the clip that must bend during installation and operation, and as such the rest of the clip can remain substantially flat throughout. Clip 11 can open either occlusally or gingivally, and as such, surfaces 23 can be either on the gingival or occlusal tie wings.

The invention is advantageous in that it rotates to open after a short initial sliding movement. This makes it more reliable after a long period of time in the mouth. The clip of the invention avoids use of springs, detents and pins, and can be fabricated from a unitary flat metal blank by conventional methods including stamping, laser cutting, and photoetching. It can be made of any of a variety of commercially available metals for making bracket clips, such as NiTi alloys, chrome cobalt, MP35N, stainless steel, and a cobalt-chromium-nickel alloy known as ELGILOY®. The bracket may be of the conventional metal kind, or could be made from single crystal ceramic or sapphire, and the clip can be coated with a tooth color coating, or made of a tooth color elastic polymer such as polyurethane and produced by molding. The thickness of the blank (and hence of the finished clip) preferably does not vary, it being more convenient to control the bending forces of the clip by varying the width of the different segments.

Figure 8:
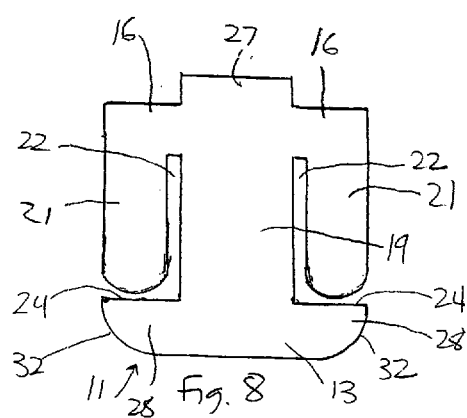
FIG. 8 is a plan view of the clip shown in FIG. 1 prior to installation.
Figure 13:
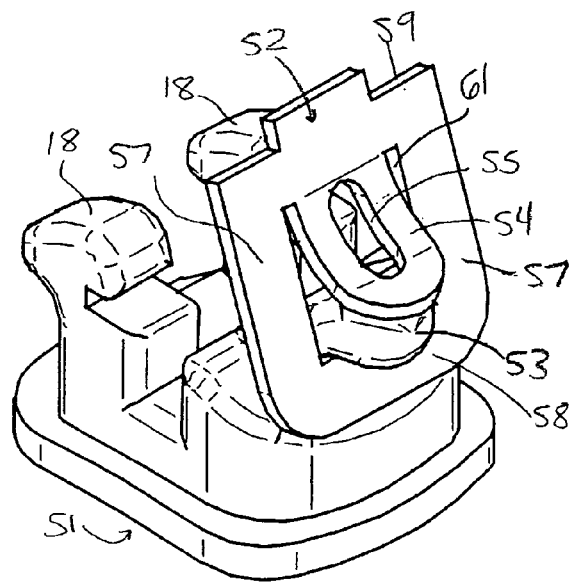
FIG. 13 is a perspective view of the bracket system shown in FIG. 9, with the clip in an open position.
Figure 16:
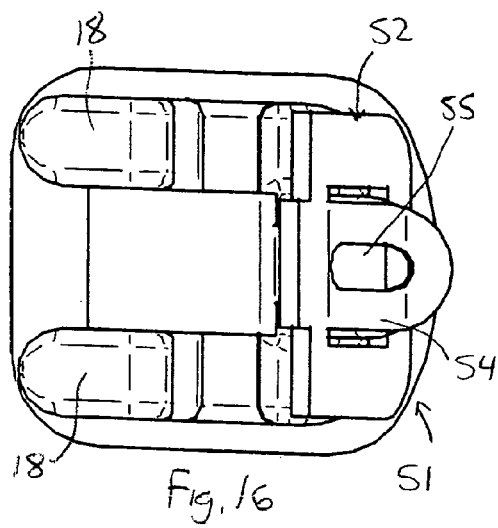
FIG. 16 is a top view of the bracket system shown in FIG. 13.
Figure 15:
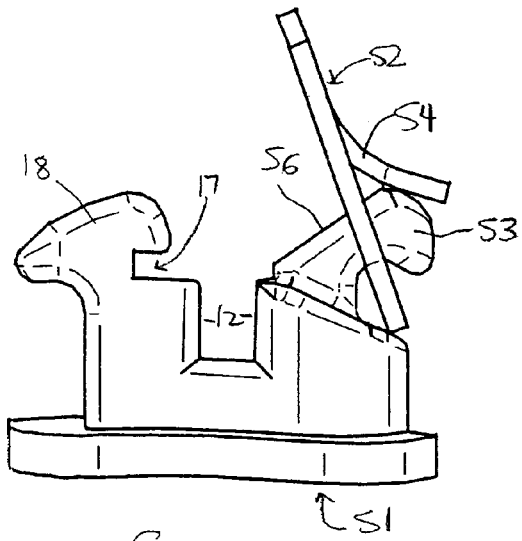
FIG. 15 is a side view of the bracket system shown in FIG. 13.
Figure 14:
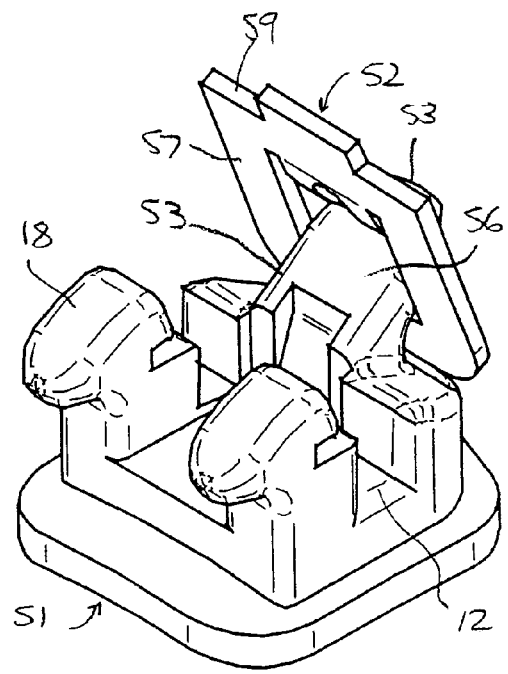
FIG. 14 is the same view as FIG. 13, viewed from a different perspective.
Figure 17:
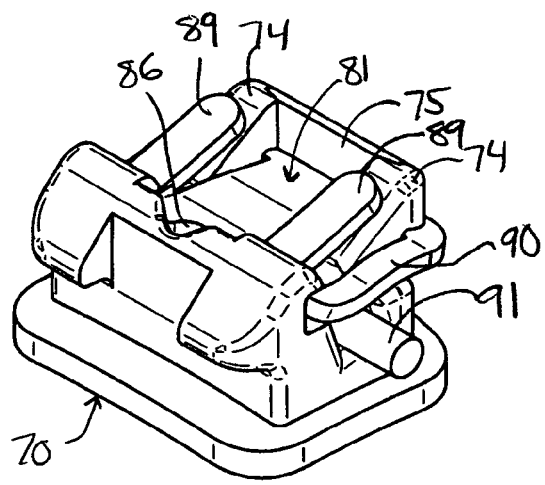
FIG. 17 is an occlusal perspective view of a bracket system according to a further embodiment of the invention, with the clip in a closed position.
Figure 18:
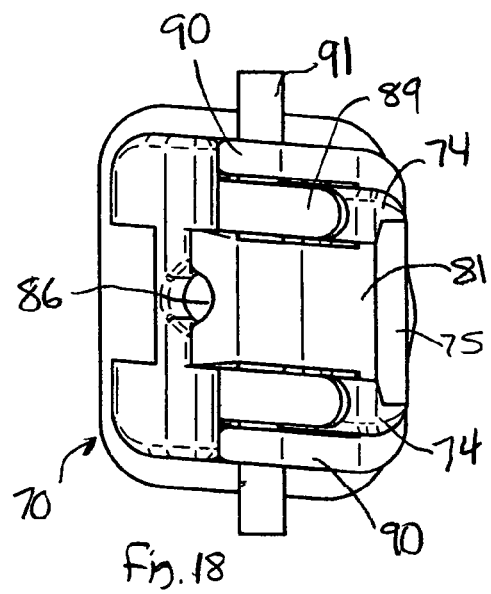
FIG. 18 is a top view of the bracket system shown in FIG. 17.
Figure 19:
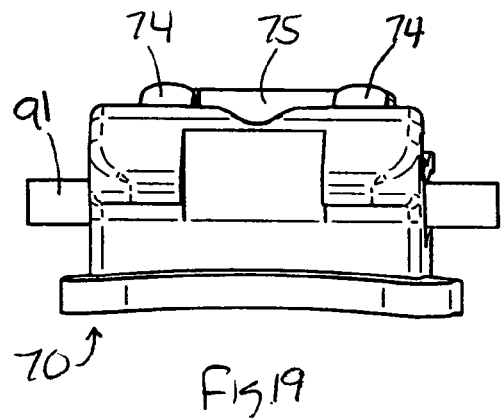
FIG. 19 is an occlusal end view of the bracket system shown in FIG. 17.
Figure 20:
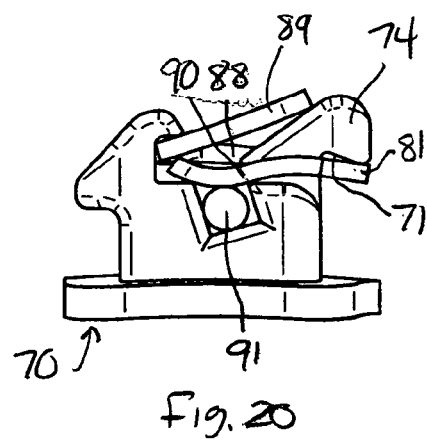
FIG. 20 is a side view of the bracket system shown in FIG. 17.
Figure 21:
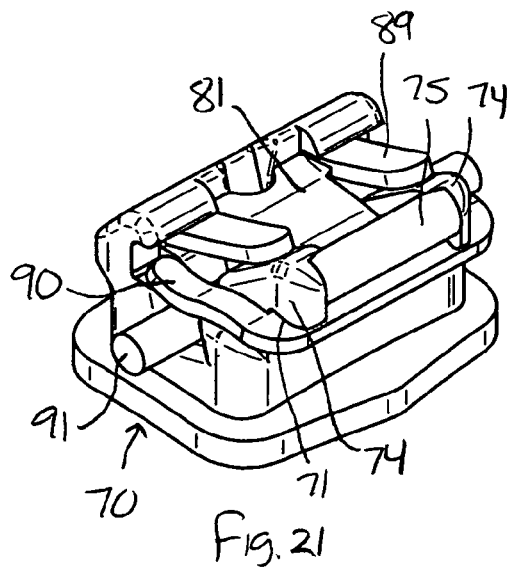
FIG. 21 is a gingival perspective view of the bracket system of FIG. 17.
Figure 22:
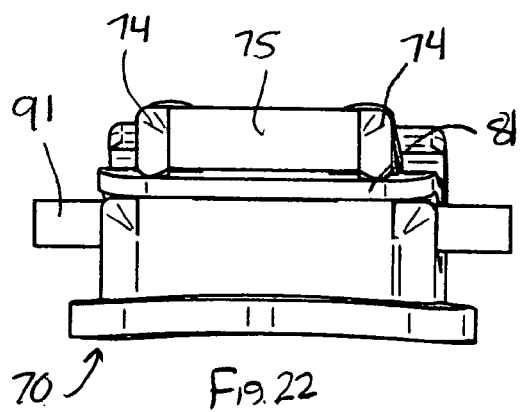
FIG. 22 is a gingival end view of the bracket system shown in FIG. 17.
Figure 23:
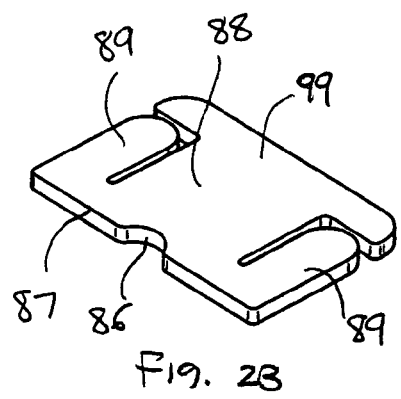
FIG. 23 is a perspective view of the clip shown in FIG. 24 prior to installation.
Figure 24:
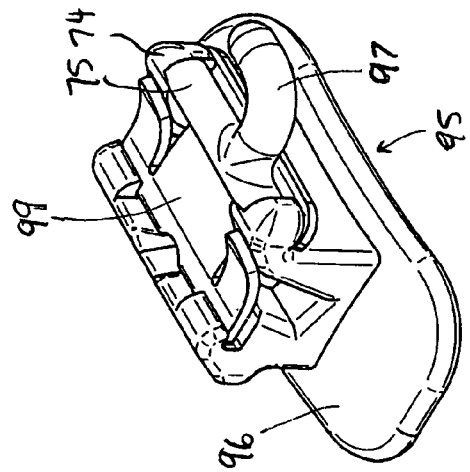
FIG. 24 is an occlusal perspective view of a bracket system according to another embodiment of the invention, with the clip in a closed position.
Figure 26:
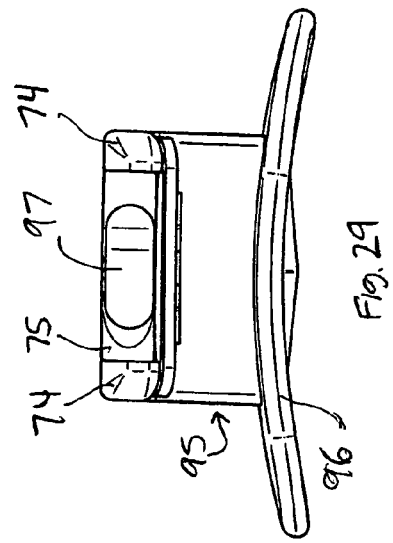
FIG. 26 is an occlusal end view of the bracket system shown in FIG. 24.
Figure 25:
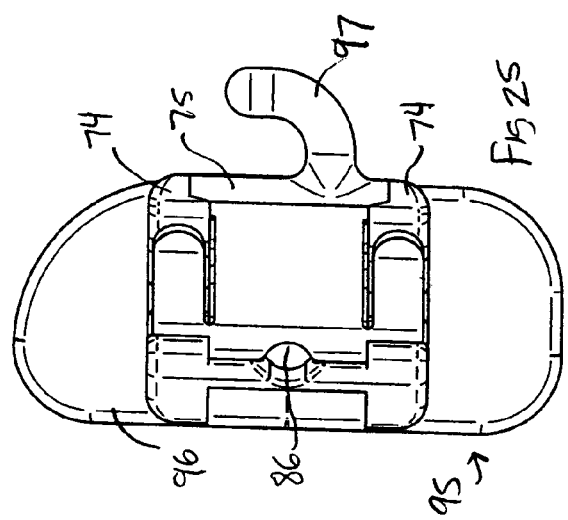
FIG. 25 is a top view of the bracket system shown in FIG. 24.
Figure 27:
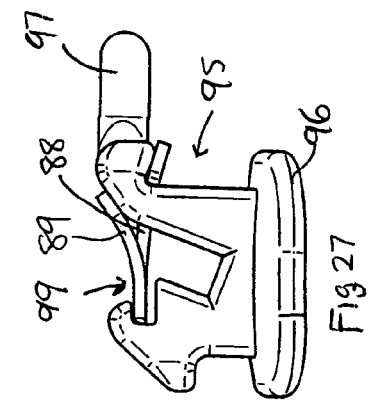
FIG. 27 is a side view of the bracket system shown in FIG. 24.
Figure 28:
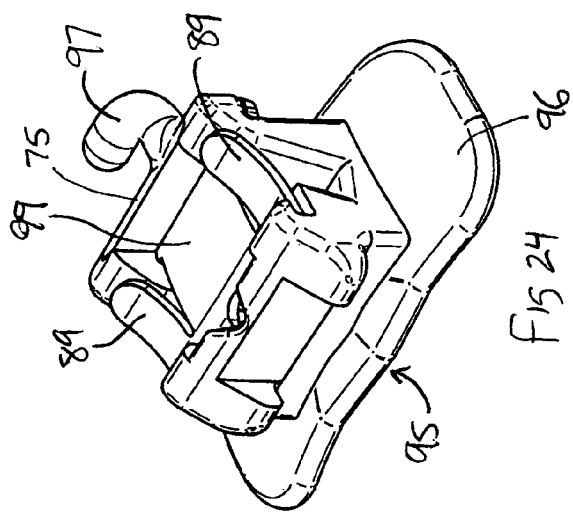
FIG. 28 is the gingival perspective view of the bracket system of FIG. 24.
Figure 29:
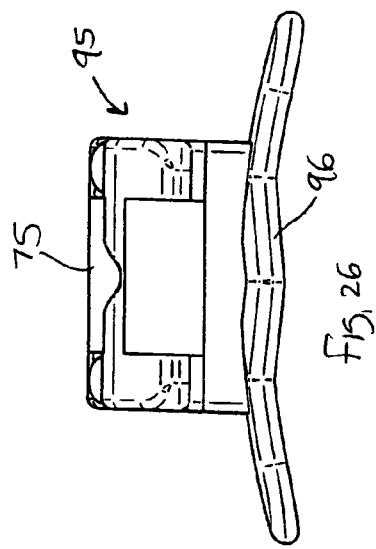
FIG. 29 is a gingival end view of the bracket system shown in FIG. 24.

As shown in FIG. 8, prior to installation on bracket 10, clip 11 is a flat sheet. Locking edge portion 16 may be straight all the way across, or may include a central rectangular projection 27 having substantially the same width as the spacing between tie wings 18. Projection 27 helps align clip 11 and secure it from sideways movement. Retaining portion 13 in this example has the same maximum width as edge portion 16 and comprises a pair of wings 28 extending sideways from mid-portion 19. Wings 28 preferably have straight inner edges 24 for engaging curved undersurfaces 31 of tie wings 14 and rounded outer edges 32 that minimize contact with the patient's mouth. Arms 21 preferably have about the same width as sloped surfaces 23 of arms 14, but could be narrower or wider if desired.

In a preferred form of the invention as shown in FIG. 7, retaining portion 13 is sufficiently long so that its outer edge 25, or an adjoining inner surface of retaining portion 13, engages a stop 30 on the bracket body 15. This mechanism prevents overrotation/overextension of clip 11 beyond the open position shown. Clip 11, once installed at the factory, is not intended to be removed from bracket 10 by the user.

Referring now to FIGS. 9 to 16, a second embodiment of a bracket system according to the invention includes a bracket 51 and clip 52. Bracket 51 is similar to bracket 10 except that bracket 51 has only a single, centrally located tie wing 53 in place of spaced tie wings 14 in the previous example. Accordingly, clip 52 has a central arm 54 which performs the function of arms 21. Arm 54 has an optional central aperture 55 that can vary in size as needed to give arm 54 a desired amount of resiliency. Tie wing 53 has an inclined surface 56 which corresponds to surfaces 23 in the previous example. Clip 52 has a retaining portion 58, a locking edge portion 59, and a pair of mid-portions 57 which cover archwire slot 12 at opposite ends. As a result of this configuration, clip 51 effectively becomes a substantially square metal sheet with a U-shaped cutout 61 that defines arm 54. This embodiment is configured for use with the less common 3-tie wing style of bracket, but functions in the same manner as described for the first embodiment.

In the preceding embodiments, the curved undercut profile of undersurfaces 31 of gingival tie wings 14 assures that the clip 11 will remain locked in use. FIGS. 17-22 illustrate a further embodiment of a bracket 70 of the invention. In this embodiment, undersurfaces 71 of tie wings 74 are substantially flat. Given this shape, it was found that the clip 81 is capable of coming loose. Accordingly, a retaining safety bar 75 is welded into place after installation of clip 81. Safety bar 75 spans the ends of tie wings 74 and locks clip 81 permanently in place. This is a preferred configuration for a bracket according to the invention that lacks sufficient curvature of the gingival tie wing undersurfaces to hold the clip in place reliably during use.

Clip 81 used in this embodiment may omit the projection 27 and instead have a central rounded notch 86 in its locking edge portion 87 to permit insertion of a tool by the clinician to unlock clip 81. Clip 81 further has a pair of additional outer spring arms 90 which extend from the retaining portion in parallel with mid-portion 88. Outer spring arms 90 may be flat, but are preferably pre-bent as by thermoforming so that they actively engage archwire 91 at opposite ends of the archwire slot.

As shown in FIGS. 23-29, self-ligating bracket and clip assemblies according to the invention can be configured for attachment to teeth at different positions in the mouth. Fixtures as needed to mount common orthodontic components can be provided as needed. A bracket 95 according to the invention has a base 96 shaped for mounting on the lower left first molar. Clip 81 is bent at both mid-portion 88 and arms 89. An L-shaped hook 97 projects from the side of safety bar 75 to permit the mounting of orthodontic elastics or NiTi springs. Clip 99 used in this embodiment is similar to clip 81, but lacks outer arms 90.

While certain embodiments of the invention have been illustrated for the purposes of this disclosure, numerous changes in the method and apparatus of the invention presented herein may be made by those skilled in the art. Such variations are within the scope of the invention as defined in the appended claims.

The invention claimed is:

1. An orthodontic bracket system comprising:
 a base contoured to engage a tooth surface;
 a body extending from the base away from the tooth surface;
 at least one first tie wing connected to the body which first tie wing extends outwardly and rearwardly therefrom and has an undersurface above the base;
 a pair of second tie wings connected to the body which extend outwardly and frontwardly therefrom, having a locking recess which opens rearwardly, and the second tie wings are spaced from the first tie wing in an occlusal-gingival direction when the bracket is mounted on a tooth;
 an archwire slot in the body extending between the first and second tie wings in a mesial-distal direction, the archwire slot located below and proximate to the locking recess in the second tie wings, wherein the first tie wing has an inclined outer surface proximate the archwire slot and on the opposite side thereof from the locking recess, which inclined outer surface extends outwardly and rearwardly therefrom; and
 a clip which comprises a flat, resilient sheet having one or more cutouts therein, one cutout forming a retaining portion configured to fit into and engage the undersurface beneath the first tie wing, a locking edge portion remote from the retaining portion that fits into the locking recess of the second tie wings, a mid-portion that spans the retaining portion and the locking edge portion and covers at least a portion of the archwire slot in a manner effective to retain an archwire therein when the clip is in a closed position wherein the locking edge portion is inserted into the locking recess and the retaining portion is engaged in the undersurface of the first tie wing, and at least one arm that extends from the locking edge portion towards the retaining portion and is spaced from the mid-portion, wherein during closing the arm rides down against the inclined rear surface of the first tie wing and bends resiliently, exerting a force that locks the locking edge portion of the clip in the recess beneath the second tie wings, and during opening the arm rides up against the inclined rear surface of the first tie wing as the locking edge portion of the clip is removed from the recess beneath the second tie wings, such that the clip remains flat during opening and closing except for bending of the resilient arm.

2. The bracket system of claim 1, wherein the bracket has a pair of first tie wings spaced apart in the mesial-distal direction and the clip has a pair of resilient arms on opposite sides configured for sliding, simultaneous engagement with the first tie wings, and the mid-portion of the clip is disposed between the resilient arms.

3. The bracket system of claim 1, wherein the inclined surface of the first tie wing defines an angle in the range of from about 45 to 70 degrees relative to a lingual-labial dimension of the archwire slot.

4. The bracket system of claim 1, wherein the clip pivots to an open position wherein the retaining portion remains in engagement with the undersurface of the first tie wing and a tip of the resilient arm engages a top surface of one of the first tie wing.

5. The bracket system of claim 1, wherein the clip has a pair of L-shaped cutouts in its sides which cutouts open laterally in opposite directions, forming the mid-portion of the clip between the cutouts and forming the arms on the sides of the cutouts opposite the midportion.

* * * * *